United States Patent [19]

Theilen

[11] 4,323,555
[45] Apr. 6, 1982

[54] METHOD OF PROTECTING CATTLE AND SHEEP AGAINST BOVINE LEUKEMIA VIRUS AND VACCINES FOR USE THEREIN

[75] Inventor: Gordon H. Theilen, Davis, Calif.

[73] Assignee: The Regents of the University of California, Berkeley, Calif.

[21] Appl. No.: 203,062

[22] Filed: Nov. 3, 1980

[51] Int. Cl.³ .......................... A61K 39/00; C12N 5/02
[52] U.S. Cl. ...................................... 424/88; 435/240; 435/241
[58] Field of Search .................. 435/240, 241; 424/88, 424/89, 95

[56] References Cited

PUBLICATIONS

Rohde et al.—Chem. Abst., vol. 88 (1978), p. 187865t.
Zebrowski et al.—Veterinary Bulletin, vol. 41, (Jul.--Dec. 1971), p. 1059, (Abst. 6652).

*Primary Examiner*—Sam Rosen

[57] ABSTRACT

Vaccines for protecting cattle against bovine leukemia virus (BLV) are prepared by in vitro culturing of lymphoid cell lines derived from bovine or ovine lymphosarcoma tissue. The cell lines are characterized by being non-producers of BLV. The vaccines and their method of preparation can also be used for protecting sheep against bovine leukemia virus.

10 Claims, No Drawings

METHOD OF PROTECTING CATTLE AND SHEEP AGAINST BOVINE LEUKEMIA VIRUS AND VACCINES FOR USE THEREIN

BACKGROUND AND PRIOR ART

Bovine leukemia (malignant lymphoma, leukosis, lymphosarcoma) is a well characterized disease of cattle and sheep. See Theilen, et al, *Veterinary Cancer Medicine,* Lea and Febiger, Philadelphia, pp. 252-272, 1979; and Straub, *A World Geography of Virus Diseases of Veterinary Importance,* Section 2-B, Chapter 17, "Enzootic Bovine Leukosis", 1980. The causal agent is the bovine leukemia virus (BLV), first described by Miller, et al (*J Natl Cancer Inst,* 43:1297, 1969). Experimentally, BLV injections readily produce infection in susceptible bovine animals (Miller, et al, *J Natl Cancer Inst,* 48:423, 1972), although tumors (malignant lymphoma) rarely result. However, in sheep, BLV will produce malignant lymphomas within 8 to 18 months (Wittmann, et al, *Arch Exp Veterinaermed,* 23:709, 1969). BLV is genetically stable and has been found to be the same all over the world, that is, one virus strain is the causative agent and "mutants" do not seem to arise in nature. Becker, Y., Bovine Leukemia Virus—A Virologist's Point of View, In: Bovine Leucosis: Various Methods of Molecular Biology, pp. 435-443, Ed. by A. Burny, Published by the Commission of the European Communities, Luxembourg (1976).

In the world there is a population of approximately 1¼ billion cattle, and in the United States and other western developed countries about 250 million of which approximately half are beef and half dairy cattle (F.A.O. Bulletin, 1978). In the USA malignant lymphomas account for 60% of dairy cattle tumors and 10% of beef cattle which is similar in other parts of the world. The incidence rates of BLV infection varies considerably among beef and dairy cattle herds, but it is estimated that a high percentage of dairy cattle in the USA are infected with BLV which is true for most parts of the world. In herds where lymphosarcomas have a high frequency, BLV infection rates will reach 80 to 90% of all the adult cattle. It appears that the larger the herd, the greater the risk for tumorous malignant lymphomas (Sorenson, et al, *Nord Vet Med Suppl I,* 16:562, 1964).

Because of the great economic loss to cattlemen is most dairy producing countries, various European (EOC) nations are attempting to erradicate BLV by "test and slaughter". Purchase of cattle or semen from infected herds, is prohibited by law. Thousands of cattle that test positive are slaughtered every week in those EOC countries that participate in the "test and slaughter" program. See Straub, O.C., *German Federal Research Institute for Animal Virus Diseases* (Bundesforschungs Anstalt fur Viruskrankheiten der Tierre, Tubingen, West Germany). It cost the British government in 1978 about 4½ million dollars in testing for BLV infection, and then paying an indemnity for 455 slaughtered cattle (*Vet. Res.,* 104:401, 1979). Comparable or greater monetary losses occur in other EOC countries. Further, there is a controversy as to the justification of such "test and slaughter" programs, and over the accuracy of the testing methods.

A more efficient way to prevent the spread of BLV infection would be through the use of vaccines. This has been recognized and some attempts have been made to develop vaccines from inactivated BLV. See, for example, Miller, et al, *Annales de Recherches Veterinaires,* 9:871, 1978. There is an obvious need for an effective vaccine to protect cattle or sheep against BLV infection, and the lymphosarcoma and leukemia caused by such infection.

SUMMARY OF INVENTION

This invention is based on the discovery that a vaccine for protecting cattle or sheep against bovine leukemia virus can be prepared from cell lines obtained by adapting cells to in vitro culture which are obtained from bovine or ovine lymphosarcoma tissue. The adapted lymphoid cells are characterized by being nonproducers of BLV. Nevertheless, these cells or antigens derived therefrom and are capable of immunizing cattle or sheep against bovine leukemia virus. The immunizing antigens are associated with the cell membrane, and may be classifiable as tumor associated transplantation antigens (TATA) and/or other antigens from the cell. Parenteral vaccines may therefore be prepared from the cells of an established cell line propagated in vitro, the cells being used either as live or inactivated cells, or the vaccines may be prepared from an extract of cell membrane protein, with or without purification to concentrate or separate the antigenic factors.

DETAILED DESCRIPTION

In practicing the method of this invention, live lymphoid cells are surgically obtained from lymphosarcoma tissue of live animals containing either active bovine leukemia virus (BLV), or from cattle or sheep not having active BLV infection but having lymphosarcoma, or are removed from such tissue shortly after death of the animal. The cells of the malignant bovine or ovine lymphoid tissue are cultured in vitro under suitable culture conditions to promote the growth of the cells.

More specifically, for example, fresh malignant bovine lymphoid tissue (lymphosarcoma tissue) or blood or bone marrow cells, obtained either by surgical biopsy or within 15 to 60 minutes after death, is minced into small pieces about 1 to 2 mm square and placed into a stationary tissue culture flask containing cell culture medium. The medium can be various standard media. Liebovitz-15(L-15) media or RPMI media is presently preferred, but other media can be used such as McCoy's medium, and others. The medium can be made or purchased already prepared from commercial companies. From 10 to 15 percent fetal calf serum is added to the medium. The cells are allowed to remain in the medium for 2 to 4 weeks until there is evidence of cellular replication (cell division) from cells in suspension. After there is good evidence of cell division, cells are transferred to new culture flasks in a concentration of about $5 \times 10^5$ cells/ml. When the cells are fully established, they can be transferred to "roller" flasks or "rocker" flasks and transferred every 2 to 3 days merely by dividing the medium into 1 or 2 parts and adding new fresh medium to old and new flasks. (See Theilen, G. H., et al: Replication of Cat Leukaemia Virus in Cell Suspension Cultures, *Nature,* 222, 589, 1969). Another suitable procedure is described in Theilen, et al, *J Natl Cancer Inst,* 40:737, 1968, which was employed to prepare cultures usable in the present invention, the BL-1 and BL-2 cell lines.

The culturing of the lymphosarcoma tissue is continued until a cell line is established capable of successive in vitro propagation. Such cell adaptation does not always occur, but it is feasible with repeated attempts. See Theilen, et al, (1968) above-cited. As reported therein, two such cell lines were established, being designated BL-1 and BL-2. Further, a third such cell line has been reported in the literature, being designated BL-3. Irvin, et al, *Nature,* 255:713, 1975. The BL-3 cell line was established from thymus and bone marrow tissue of a 3 month old Hereford male calf with lymphosarcoma. Some properties of such cell lines have heretofore been determined and published. The adapted cells are usually characterized by a hyperdiploid chromosome pattern, however occasionally a hypodiploid or cell line with aneuploidy are described. Normal bovine chromosomal pattern is 58 autosomes and 2 sex chromosomes while the established cell lines (BL-1 and BL-2 have a hyperdiploid number of more than 60 (mainly 63–65). The cytogenetic pattern of BL-3 has a hypodiploid (mainly 57–59) and some cells with a normal chromosomal complement. Most established lines have the same number of chromosomes as found in the lymphosarcoma tissue, blood or bone marrow cells from which the cell line was established. The BL-3 cell line has been deposited with the American Type Culture Collection, Rockville, Md., and has been assigned the ATCC Deposit No. CRL-8037.

A heretofore unpublished characteristic of the lymphoid cell lines used in practicing the present invention is that they are non-producers of BLV. In other words, the propagation of the cells in vitro does not result in the formation of bovine leukemia virus and the cells are non-infective for cattle or sheep. Underlying the present invention is the finding that such non-producer cells provide antigens which have immunizing activity against bovine leukemia virus infection. The immunizing antigens are associated with the surfaces of the cell membranes, and are probably classifiable as tumor associated transplantation antigens (TATA). Although such cell lines are non-producers of BLV, Irvin, et al found that the cell line BL-3 will produce tumors in immune deficient athymic nude mice: *Nature,* 255:713, 1975. The mechanism of protection of the vaccines prepared in accordance with this invention has not as yet been elucidated. The vaccines may act by directly blocking the viral infection in susceptible host cells, or by cellular immune surveillance whereby the hosts immunocytes recognize newly infected cells and "kill" them after early infection. What has been found is that little or no viremia results when cattle are exposed to BLV after vaccination.

For commercial purposes, the adapted lymphoid cell line may be propagated and harvested as previously described. Commercial production could utilize the same principles, although much larger containers would be used, such as vats that hold several hundred to thousands of liters of culture medium, or on roller bottle or rocker flask assembly lines.

As described above, the propagated cells may be harvested without killing the cells. Further, they may be stored in frozen condition, for example, the cells may be stored alive in liquid nitrogen. Cells can be stored alive at $-70°$ C. to $-180°$ C. (liquid nitrogen temperatures) by freezing them in sealed containers (vials) that contain 10% dimethylsulfoxide (DMSO), 13% fetal calf serum, and 77% culture medium with a final cell concentration of $5 \times 10^5$ to $1 \times 10^7$ cells/ml. The cells may also be lyophilized for non-frozen storage, either for use as a vaccine containing most or all of the cellular antigens, or for preservation to be used later in preparing a vaccine. For preservation as live cells, the cells should be frozen in calf serum and DMSO, and stored at $-70°$ to $-80°$ C., or at liquid nitrogen temperatures of about $-180°$ C. For use as a vaccine, the live non-BLV producer lymphoid cells may be combined with a suitable adjuvant such as aluminum hydroxide gel. The cattle or sheep may be vaccinated with vaccine doses of $5 \times 10^6$ to $2 \times 10^7$ of live cells. A sequence of vaccinations is preferred, such as 2 to 3 vaccinations at intervals of 2 to 3 weeks. The vaccines may be administered by one of several known parenteral injection procedures, such as subcutaneously or intradermally, or a combination of such routes of injection.

In an alternate procedure, the lymphoid cells may be used in a vaccine in killed form. For example, the vaccine may be prepared by inactivating the cells as described by Pedersen, et al, *Am. J. Vet. Res.,* 40, 1120–1126 (1978). The inactivated cells are combined with a suitable adjuvant and are administered in dose form, using the same cell concentrations and dose procedures described above for the live cells. Such vaccines have the advantage of being storable under non-frozen condition. For example, the killed cells may be lyphilized, and packaged in one vial, and the adjuvant solution in a second vial for combination with the cells immediately prior to administration. It is also possible to add adjuvant to live cells and store in a sealed vial at room temperature or at 4° C. for several months. Cell membrane antigens are shown to be preserved by this method.

The lymphoid cells may also be used to prepare a vaccine by a procedure in which the cells are extracted with an aqueous solution of a non-ionic detergent. The extraction solubilizes the cell membrane protein. After separation of the cell residue from the supernatant, the supernatant solution can be used to prepare the vaccine, since it will contain immunizing antigens. The solution may be used as such if the antigens are sufficiently concentrated therein, or the solubilized protein may be recovered and concentrated, or subjected to purification to obtain the immunizing antigens in more active form. Since such procedures are well known, they need only be described generally herein. For example, on completion of the propagation, the cells may be separated from the liquid media by centrifugation. The separated cells are then extracted with a non-ionic detergent which solubilizes the membrane-associated protein. For example, Triton X-100 (octyl phenoxy polyethoxyethanol) can be used, which is distributed commercially by Sigma Chemical Co., St. Louis, Mo., or Nonidet P 40, which is distributed by Gallard-Schlesinger Chemical Mfg. Corp., Carle Place, N.Y. Such non-ionic detergents are capable of solubilizing membrane protein without appreciable denaturation of the protein, and use of such extractions at concentrations of from about 0.4 to 0.6%.

The present invention is further illustrated by the following examples.

EXAMPLE I

A vaccine for protecting cattle against bovine leukemia virus was prepared as follows:

BL-3 (ATCC No. CRL-8037) cells were propagated in L-15 medium (Liebovitz-15) or RPMI 1640 containing 15 percent fetal calf serum and penicillin and streptomycin and grown in cell suspension. Cells were harvested by centrifugation at 1,200 RPM and washed 3 times in phosphate buffered saline (PBS) and then resuspended in 2.0 ml of PBS at a concentration of $1 \times 10^7$ cells. The vaccine was held at 4° C. (on ice) until used within 1 to 3 hours. Cattle were injected with 1 ml subcutaneously and 1 ml intramuscularly. Two and four weeks later vaccinated cattle were injected with the same amount of cells in PBS according to the procedure above with 0.2 ml of Alhydrogel (aluminum hydroxide) added and adjusted to a pH of 7.2.

EXAMPLE II

Vaccines prepared as described in Example I were tested as follows:

Animals—Twelve 6 to 8 month old Hereford crossbred calves were housed in a feed lot as part of a feed lot nutritional trial. The 12 calves selected for the experiment were housed randomly with 68 other calves not part of the trial. The 12 experimental calves were separated before vaccination testing into three groups. Group 1 consisted of 5 calves that were to be vaccinated and at 16 weeks post-vaccination callenged with active BLV; Group 2 consisted of 3 calves that were vaccinated and not challenged; and Group 3 consisted of 4 calves not vaccinated but injected three times with buffered culture media. The experimental protocol is summarized in Table A.

TABLE A

| GROUP I Vaccinated & Challenged | GROUP II Vaccinated & Not Challenged | GROUP III Not Vaccinated & Challenged |
|---|---|---|
| 808 | 814 | 822 |
| 832 | 823 | 834 |
| 818 | 860 | 842 |
| 836 |  | 868 |
| 878 |  |  |

Pre-testing for Status of BLV Infection—The presence of BLV virus infection was determined by the immune diffusion test (ID) for BLV antibodies, by radioimmune assay (RIA) for inhibition of structural protein p24 and by syncytial assay (SYN) for presence of BLV infection in peripheral blood lympocytes. Pre-testing assays were conducted twice, two weeks before and at time of vaccination.

Vaccination Procedure—Cattle were vaccinated at 2 week intervals for a total of three vaccinations by use of $1 \times 10^7$ live BL-3 cells (ATCC No. CRL-8037) in 2.0 ml of phosphate buffered saline (PBS) and 2nd and 3rd vaccinations contained in addition 0.2 ml of Alhydrogel (aluminum hydroxide) adjusted to pH 7.2 as an adjuvant. Each vaccinated animal received one-half of each vaccine dose subcutaneously and one-half intradermally.

Challenge with Virulent BLV—Two weeks after the 3rd vaccination, Groups 1 and 2 were inoculated with 250,000 lymphocytes infected with live BLV.

Evaluation of Vaccine Results—Blood was collected before the 2nd and 3rd vaccinations and at 2 week intervals, after challenge, for 11 weeks (4 samples), for determination of antibodies against BLV and for presence of infective BLV.

Results—The results as summarized in Table B, demonstrate the BLV pre-vaccine infection and antibody status based on two samples for each animal at 2 weeks before and day of vaccination, and BLV infection and antibody status 11 weeks after BLV challenge. Animals 832 (Group 1) and 842 (Group 3) were positive on all tests before vaccination and throughout the 18 weeks of the vaccine trial. The other animals were negative on all tests before vaccination. At 16 weeks post vaccination and 11 weeks after BLV challenge no vaccinated animals (Groups 1 and 2) negative at time of vaccination were positive for BLV infection although 2 of 3 unvaccinated negative animals (834 and 868) became positive after challenge. The results of this experiment indicated that vaccinated cattle were protected 11 weeks after experimental challenge against BLV (Group 1), and cattle not challenged did not acquire a contact infection (Group 2). Non-vaccinated cattle inoculated with BLV had a great risk for virus infection.

TABLE B

| Group of Animal Nos. | Pre-Vaccine | | | 16 Weeks Post-Vaccinated and 11 Weeks Post-Challenge | | |
|---|---|---|---|---|---|---|
|  | ID[a] | RIA[b] | SYN[c] | ID[a] | RIA[b] | SYN[c] |
| GROUP I: Vaccinated-Challenged |  |  |  |  |  |  |
| 808 | − | − | − | − | − | − |
| 818 | − | − | − | +/− | − | − |
| 832 | + | + | + | + | + | + |
| 836 | − | − | − | +/− | − | − |
| 878 | − | − | − | − | − | − |
| GROUP II: Vaccinated-Not Challenged |  |  |  |  |  |  |
| 814 | − | − | − | − | − | − |
| 823 | − | − | − | − | − | − |
| 860 | − | − | − | − | − | − |
| GROUP III: Not Vaccinated-Challenged |  |  |  |  |  |  |
| 822 | − | − | − | − | − | − |
| 834 | − | − | − | + | + | + |
| 842 | + | + | + | + | + | + |
| 868 | − | − | − | + | + | + |

[a]ID - Immunodiffusion to measure BLV antibodies.
[b]RIA - Radioimmunoassay p24 inhibition.
[c]SYN - Virus syncytium assay.

EXAMPLE III

The BLV non-producer lymphoid cells may be extracted to obtain protective proteins isolated from the cell membranes. One suitable procedure would include the following steps:

(1) The lymphoid cells are grown in suspension culture and stored at 70° C. or large batches of unfrozen cells are used as source of cell membranes.

(2) Cell membranes are extracted by homogenizing cells at 4° C. with lysis buffer (20 mM Tris-HCl, 0.075 M NaCl, 0.5% Triton X-100, and 0.7% Trasylol, a proteinase enzyme) at a ratio of one volume lysis buffer to one volume cells. The lysis continues for 30 minutes at 4° C. by gentle agitation.

(3) Add 20% S-DOC to lysis buffer at a final concentration of 0.5% for 10 minutes at 4° C.

(4) Add PBS to make a final 10% cell extract.

(5) Centrifuge one (1) hour at 100,000×g at 4° C.

(6) Save the supernatant fluid which contains the solubilized glycoprotein cell membrane antigens.

(7) A protein determination is made and each animal is vaccinated with 5 to 10 mg of protein for 2 to 3 vaccinations.

The reagents and commercial sources as used in the foregoing procedure are further identified as follows:

Triton X-100, Sigma Chemical Co., St. Louis, Missouri; Trasylol, Bayers Laboratories, Leverkusen, West Germany; S-Doc, Sodium desoxycholate ($C_{27}H_{39}NaO_4$), Merck Laboratories, Rahway, New Jersey; and PBS, phosphate buffered saline.

I claim:

1. The method of protecting cattle or sheep against bovine leukemia virus (BLV), comprising culturing lymphoid cells in vitro obtained from bovine or ovine lymphosarcoma tissue, continuing said culturing until a cell line is established capable of successive in vitro propagation, which cell line is characterized by being a non-producer of BLV, propagating said cells in vitro, harvesting the propagated cells, and preparing a parenteral vaccine therefrom for administration to cattle or sheep.

2. A vaccine prepared by the method of claim 1.

3. A vaccine prepared by the method of claim 1 in which said cells are live and are combined with an adjuvant.

4. The method of claim 1 or the vaccines of claim 2 or 3 in which said cells line is identified by ATCC No. CRL-8037.

5. The method of claim 1 in which said vaccine is prepared by extracting the harvested cells with an aqueous solution of a non-ionic detergent to obtain a solution of cell membrane protein.

6. A vaccine prepared by the method of claim 5 in which the viral membrane protein is combined with an adjuvant.

7. The method of claim 5 or the vaccine of claim 6 in which said cell line is identified by ATCC No. CRL-8037.

8. The method of protecting cattle against bovine leukemia virus (BLV), comprising culturing lymphoid bovine cells in vitro obtained from bovine lymphosarcoma tissue, continuing said culturing until a cell line is established capable of successive in vitro propagation, which cell line is characterized by a aneuploid or normal chromosome pattern and by being a non-producer of BLV, propagating said cells in vitro, harvesting the propagated cells without killing the cells, and preparing a parenteral vaccine from the live cells by combining them with an adjuvant.

9. A vaccine prepared by the method of claim 8.

10. The method of claim 8 or the vaccine of claim 9 in which said cell line is identified by ATCC No. CRL-8037.

* * * * *